United States Patent
Mikkelsen et al.

(10) Patent No.: US 10,835,483 B2
(45) Date of Patent: Nov. 17, 2020

(54) ANTIPERSPIRANT STICK COMPOSITIONS

(71) Applicant: Henkel IP & Holding GmbH, Duesseldorf (DE)

(72) Inventors: Tyler Mikkelsen, Scottsdale, AZ (US); Sofia Carolina Herrera, Scottsdale, AZ (US); Nancy Rodgers, Chandler, AZ (US)

(73) Assignee: Henkel IP & Holding GmbH

( * ) Notice: Subject to any disclaimer, the term of this patent is extended or adjusted under 35 U.S.C. 154(b) by 0 days.

(21) Appl. No.: 15/729,280

(22) Filed: Oct. 10, 2017

(65) Prior Publication Data

US 2019/0105255 A1 Apr. 11, 2019

(51) Int. Cl.

| | |
|---|---|
| *A61K 8/02* | (2006.01) |
| *A61K 8/26* | (2006.01) |
| *A61K 8/27* | (2006.01) |
| *A61K 8/28* | (2006.01) |
| *A61K 8/31* | (2006.01) |
| *A61K 8/92* | (2006.01) |
| *A61K 8/365* | (2006.01) |
| *A61K 8/891* | (2006.01) |
| *A61Q 15/00* | (2006.01) |
| *A61K 8/81* | (2006.01) |
| *A61K 8/37* | (2006.01) |
| *A61K 8/58* | (2006.01) |
| *A61K 8/34* | (2006.01) |

(52) U.S. Cl.
CPC ............ *A61K 8/92* (2013.01); *A61K 8/0229* (2013.01); *A61K 8/26* (2013.01); *A61K 8/27* (2013.01); *A61K 8/28* (2013.01); *A61K 8/31* (2013.01); *A61K 8/342* (2013.01); *A61K 8/365* (2013.01); *A61K 8/37* (2013.01); *A61K 8/585* (2013.01); *A61K 8/8111* (2013.01); *A61K 8/891* (2013.01); *A61K 8/922* (2013.01); *A61K 8/927* (2013.01); *A61Q 15/00* (2013.01)

(58) Field of Classification Search
CPC ... A61K 8/02; A61K 8/26; A61K 8/27; A61K 8/28; A61K 8/31; A61K 8/81; A61K 8/92; A61K 8/365; A61K 8/891; A61Q 15/00

See application file for complete search history.

(56) References Cited

U.S. PATENT DOCUMENTS

| | | |
|---|---|---|
| 4,511,554 A | 4/1985 | Geria et al. |
| 8,691,250 B2 | 4/2014 | Urban et al. |
| 2009/0304617 A1* | 12/2009 | Banowski ............... A61K 8/02 424/68 |
| 2011/0038823 A1* | 2/2011 | Phipps ................... A61K 8/06 424/68 |
| 2012/0156152 A1 | 6/2012 | Bianchi |
| 2014/0271514 A1 | 9/2014 | Sturgis et al. |
| 2014/0271515 A1 | 9/2014 | Sturgis et al. |
| 2017/0007515 A1 | 1/2017 | Menon et al. |

FOREIGN PATENT DOCUMENTS

WO 2011050044 A1 4/2011

OTHER PUBLICATIONS

PCT International Search Report & Written Opinion PCT/US2018/052111 Completed: Jan. 31, 2019 dated Jan. 31, 2019 18 pages.

* cited by examiner

*Primary Examiner* — Zohreh A Fay
(74) *Attorney, Agent, or Firm* — P. Scott Smith

(57) ABSTRACT

An antiperspirant stick composition can include a synthetic wax having a melting point of less than or equal to 90° C., a melting point additive present at a weight ratio to the synthetic wax to provide the composition with a melting point greater than or equal to 40° C., an effective amount of an antiperspirant active agent, and less than 2 wt % hydrogenated oils, petrolatum, 12-hydroxystearic acid, polyethylenes having a melting point greater than or equal to 60° C., and combinations thereof.

13 Claims, 1 Drawing Sheet

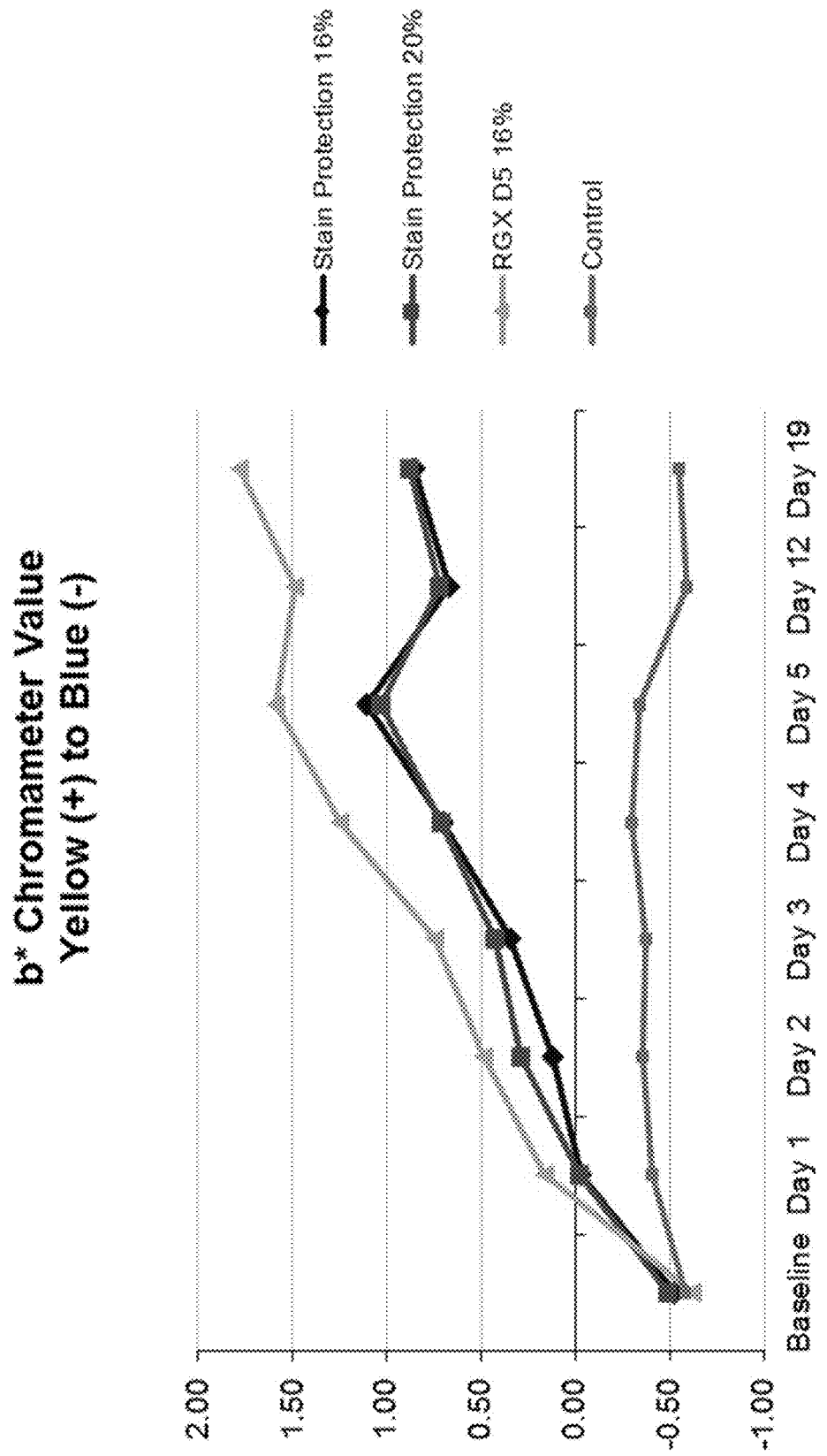

US 10,835,483 B2

ANTIPERSPIRANT STICK COMPOSITIONS

BACKGROUND

Sweating is an important physiological function that helps protect the body from overheating. There are millions of sweat glands distributed over the human body. The majority of sweat glands are "eccrine" sweat glands, which are found in large numbers on the soles of the feet, the palms of the hands, the face, and in the armpits. Eccrine glands secrete an odorless, clear fluid that helps the body control its temperature by promoting heat loss through evaporation. Another type of sweat gland is called the "apocrine" gland. Apocrine glands are found in the armpits, chest, and genital region. They produce a thick, oily fluid that produces a characteristic body odor when it comes into contact with bacteria on the surface of the skin. Thus, while sweating is an important physiological function, it can also cause embarrassing body odor, wet clothing, and wet skin.

Antiperspirant compositions are a first line of defense against, or treatment for, excessive sweating of the underarms, hands, feet, etc. Typically, antiperspirants are applied to the skin to plug sweat ducts and reduce wetness at the areas of application. For example, when an antiperspirant is applied to the skin, the antiperspirant active ingredients can dissolve in the sweat or moisture on the skin surface. The dissolved components of the antiperspirant can form a small plug near the top of the sweat gland, which can reduce the amount of sweat that is secreted to the skin surface. Additionally, because perspiration stimulates odor-causing bacteria, antiperspirants also help reduce body odor. Antiperspirant compositions are available in a variety of forms, such as sticks, sprays, gels, roll-ons, etc.

BRIEF DESCRIPTION OF THE DRAWINGS

For a fuller understanding of the nature and advantage of the present invention, reference is being made to the following detailed description of preferred embodiments and in connection with the accompanying drawings, in which:

FIG. 1 is a graph illustrating staining properties of various formulations of antiperspirant stick compositions.

DESCRIPTION OF EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a polymer" can include a plurality of such polymers.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 milligrams to about 80 milligrams" should also be understood to provide support for the range of "50 milligrams to 80 milligrams." Furthermore, it is to be understood that in this written description support for actual numerical values is provided even when the term "about" is used therewith. For example, the recitation of "about" 30 should be construed as not only providing support for values a little above and a little below 30, but also for the actual numerical value of 30 as well.

As used herein, "effective amount" refers to an amount of an ingredient which, when included in a composition, is sufficient to achieve an intended compositional or physiological effect. Thus, in the context of an active agent, an "effective amount" refers to a non-toxic, but sufficient amount of the active agent, to achieve therapeutic results in treating a condition for which the active agent is effective. It is understood that various biological factors may affect the ability of a substance to perform its intended task. Therefore, an "effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

As used herein, all amounts recited in terms of weight percent, weight percentage, percent by weight, and the like (e.g. wt % or w/w %) refer to weight percentages with respect to the total amount of a composition, unless otherwise specified. Furthermore, a "weight ratio" refers to amounts based on weight percent.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

As described above, sweating is an important physiological condition that helps regulate body temperature. However, sweating can also cause embarrassing body odor, wet skin, and wet clothing. As such, antiperspirant compositions can act as a first line of defense against excessive or normal sweating. However, antiperspirant compositions are known to cause discoloration of textiles that come into contact with the composition. This can also cause embarrassment to a user of antiperspirants. In some cases, it can further cause additional expense to replace permanently discolored clothing.

The present disclosure describes effective antiperspirant stick compositions that can help reduce or minimize the discoloration of textiles that come into contact with the composition. For example, one cause of induced discoloration of textiles due to contact with an antiperspirant composition can result from specific components used the antiperspirant formulation. Therefore, minimizing or eliminating highly discoloring components from the formulation can reduce or minimize the discoloration of textiles that come into contact with the composition.

In another example, the mere process of sweating can facilitate discoloration of textile materials, especially in the presence of antiperspirant active agents. Thus, in some examples, it can be beneficial to include a sweat-sequestering agent in the formulation. In some examples, the sweat-sequestering agent can reduce or minimize the amount of sweat that reaches the textile material. In additional examples, the sweat-sequestering agent can facilitate removal of sweat and/or other components of the formulation from the textile material.

It is further noted that by either minimizing highly discoloring components in the formulation, or by including a sweat-sequestering agent in the formulation, or both, it is possible to include an effective amount of an antiperspirant active agent while still reducing or minimizing the staining potential of the composition. This is in contrast to formulations where the discoloring properties have been reduced by lowering the amount of antiperspirant active agent in the formulation.

As will become more apparent from the present description, the present antiperspirant stick compositions can be prepared in a number of ways. A few specific, but non-limiting, examples are provided below. For example, in some cases, an antiperspirant stick composition can include a synthetic wax having a melting point of less than or equal to 90° C., a melting point additive present at a weight ratio to the synthetic wax to provide the composition with a melting point greater than or equal to 40° C., and an effective amount of an antiperspirant active agent. The composition can also include less than 2 wt % hydrogenated oils, petrolatum, polyethylenes having a melting point greater than or equal to 60° C., 12-hydroxystearic acid, the like, and combinations thereof.

In other examples, the antiperspirant stick composition can include an amount of a synthetic wax having a melting point less than or equal to 90° C., a melting point additive in an amount sufficient to provide the composition with a melting point greater than or equal to 40° C., a fatty alcohol, and an effective amount of an antiperspirant active agent. The fatty alcohol and the antiperspirant active agent can be present at a weight ratio of from 2:1 to 1:2.

In yet other examples, the antiperspirant stick composition can include a synthetic wax, a fatty alcohol, a hydrophilic surfactant, a plasticizer, and an effective amount of an antiperspirant agent. In some examples, the hydrophilic surfactant can have a hydrophilic-lipophilic balance (HLB) value greater than 10 and can be present in an amount sufficient to minimize perspiration-induced discoloration of fabric in contact with the composition. Further, the plasticizer can be present in an amount effective or sufficient to minimize hardening of the composition due to contact with an aqueous composition. Additionally, the fatty alcohol and the antiperspirant active agent can be present at a weight ratio of from 2:1 to 1:2.

In still other examples, the antiperspirant stick composition can include a synthetic wax having a viscosity of from about 0.1 centipoise (cps) to about 20 cps at a temperature of 99° C., a hydrophilic surfactant having an HLB value greater than 10, a plasticizer, and an effective amount of an antiperspirant active agent. The hydrophilic surfactant can be present in an amount sufficient to minimize perspiration-induced discoloration of fabric in contact with the composition. Additionally, the plasticizer can be present in an amount sufficient to minimize hardening of the composition due to contact with an aqueous composition.

With these non-limiting examples in mind, antiperspirant stick compositions will be described in further detail. Antiperspirant stick compositions can generally include a variety of ingredients, such as structurants (e.g. primary structurants, secondary structurants, etc.), lubricants, masking agents, emollients, bulking agents, active agents, and the like.

The structurants in stick compositions can also be characterized as carriers for the antiperspirant active agent. Primary structurants typically can include any number of compounds or agents that are suitable to help provide and maintain the basic structure and shape of the antiperspirant stick while preventing or minimizing the crystallinity of the stick. Thus, in some examples, the primary structurant can help impart structural integrity to the stick composition that is sufficient to withstand typical forces during application of the composition to the skin of a user. Force can be measured using a texture analyzer (e.g. model TAxT2i, or other suitable texture analyzer). The texture analyzer typically uses a load cell that measures the force required for fracture of the stick composition. Typically, the type and amount of the primary structurant can provide a stick composition that fractures at a force of from about 100 g/cm$^2$ to about 400 g/cm$^2$, about 100 g/cm$^2$ to about 200 g/cm$^2$, 200 g/cm$^2$ to about 300 g/cm$^2$, or from about 300 g/cm$^2$ to about 400 g/cm$^2$.

Non-limiting examples of primary structurants can include fatty acids (or an ester thereof) having from about 8 to about 26 carbon atoms, fatty alcohols (or an ester thereof) having from about 8 to about 26 carbon atoms, natural or synthetic waxes having from about 8 to about 90 carbon atoms, the like, or combinations thereof. In some examples, the primary structurant can have a melting point in the range of about 30° C. to about 90° C., or from about 35° C. to about 70° C.

In some specific examples, the primary structurant can include a fatty alcohol, or an ester thereof. Where the primary structurant includes a fatty alcohol, the fatty alcohol can be or include a saturated or unsaturated $C_8$ to $C_{26}$ fatty alcohol. In other examples, the fatty alcohol can be or include a saturated or unsaturated $C_{10}$ to $C_{22}$ fatty alcohol, or a saturated or unsaturated $C_{14}$ to $C_{20}$ fatty alcohol. In yet additional examples, the fatty alcohol can be or include lauryl alcohol, myristyl alcohol, cetyl alcohol, stearyl alcohol, arachidyl alcohol, behenyl alcohol, or a combination thereof. In further specific examples, the fatty alcohol can be or include stearyl alcohol. In some other specific examples, the fatty alcohol can be or include cetyl alcohol.

The primary structurant can be present in the antiperspirant stick composition in a variety of amounts, depending on the particular structurant employed. In some examples, the primary structurant can be present in the antiperspirant stick composition in an amount from about 12 wt % to about 25 wt %. In yet other examples, the primary structurant can be present in the composition in an amount from about 14 wt % to about 22 wt %, or from about 16 wt % to about 20 wt %.

In some examples, the antiperspirant stick composition can further include a secondary structurant. In some examples, secondary structurants can further minimize or prevent crystallinity of the stick composition. Typically, secondary structurants can increase the cohesiveness, flexibility, and/or stability of the stick composition. For example, in some cases, a very rigid stick composition formulated using only a primary structurant can have lower slip and can feel like it is dragging during application to the skin. Thus, in some examples, a secondary structurant can help improve the experience of the user during application by providing increased slip to the stick composition as compared to a composition only employing a primary structurant. In some additional examples, the addition of a secondary structurant can also provide added stability to the stick composition by decreasing the degree of syneresis (i.e. expulsion or loss of liquids from the composition) as compared to a stick composition employing only a primary structurant. Further, in some examples, secondary structurants can help control or maintain the melting temperature of the stick composition to provide increased thermal stability during storage and/or transportation of the stick composition as compared to a stick composition employing only a primary structurant. Moreover, secondary structurants can be suitable to help provide and maintain the basic structure and shape of the antiperspirant stick.

Non-limiting examples of secondary structurants can include fatty acids (or an ester thereof) having from about 8 to about 26 carbon atoms, fatty alcohols (or an ester thereof) having from about 8 to about 26 carbon atoms, natural or synthetic waxes having from about 8 to about 90 carbon atoms, alkyl silicone waxes, the like, or combinations thereof. In some examples, the primary structurant can have a melting point in the range of about 30° C. to about 90° C., or from about 35° C. to about 80° C.

In some specific examples, the secondary structurant can include a fatty alcohol, or an ester thereof, that is different from any fatty alcohol used as a primary structurant in the formulation. Where the secondary structurant includes a fatty alcohol, the fatty alcohol can be or include a saturated or unsaturated $C_8$ to $C_{26}$ fatty alcohol. In some other examples, the fatty alcohol can be or include a saturated or unsaturated $C_{10}$ to $C_{22}$ fatty alcohol, or a saturated or unsaturated $C_{14}$ to $C_{20}$ fatty alcohol. In some specific examples, the fatty alcohol can be or include lauryl alcohol, myristyl alcohol, cetyl alcohol, stearyl alcohol, arachidyl alcohol, behenyl alcohol, or a combination thereof. In some other specific examples, the fatty alcohol can be or include cetearyl alcohol. In additional specific examples, the fatty alcohol can be or include cetyl alcohol. Further, where the secondary structurant is or includes a fatty alcohol, the fatty alcohol can typically be present in the composition in an amount from about 0.1 wt % to about 4 wt %, or from about 0.5 wt % to about 2 wt %. In some additional examples, the secondary structurant can be or include fully or partially hydrogenated oils, such as hydrogenated soybean oil, hydrogenated castor oil, hydrogenated plant oils, the like, or combinations thereof. Secondary structurants can also include petrolatum, triglycerides, polyethylenes having a melting point greater than or equal to 60° C., 12-hydroxystearic acid, alkyl silicone waxes, and a variety of other suitable secondary structurants.

In some examples, the secondary structurant can be or include a hydrogenated oil, petrolatum, 12-hydroxystearic acid, a polyethylene having a melting point greater than or equal to 60° C., the like, or a combination thereof. However, these particular secondary structurants can also be highly discoloring of textile materials. As such, in some examples, the antiperspirant stick compositions can include less than 2 wt %, less than 1.5 wt %, less than 1 wt %, or less than 0.5 wt % hydrogenated oils (e.g. fully or partially hydrogenated soybean oil, fully or partially hydrogenated castor oil, fully or partially hydrogenated plant oils, the like, or combinations thereof), petrolatum, 12-hydroxystearic acid, a polyethylene having a melting point greater than or equal to 60° C., and combinations thereof. In some specific examples, the antiperspirant composition can include no, or substantially no, hydrogenated oils, petrolatum, 12-hydroxystearic acid, polyethylenes having a melting point greater than or equal to 60° C. and combinations thereof.

In additional examples, the secondary structurant can be or include a synthetic wax. However, synthetic waxes can typically have relatively high melting points. Such high-melting-point waxes, in some cases, can cause the antiperspirant stick composition to feel hard and can make it challenging to deliver the composition and antiperspirant active agent to the skin. Thus, where a synthetic wax is employed as a secondary structurant, the synthetic wax can have a melting point of less than or equal to 90° C. In yet other examples, the synthetic wax can have a melting point less than or equal to 80° C., or less than or equal to 70° C.

A variety of synthetic waxes can be used. In some examples, whether a particular synthetic wax is suitable for use in the present formulations can depend on the solubility of the synthetic wax in, or compatibility of the synthetic wax with, other ingredients in the formulations at a reasonably low temperature. This can help decrease processing temperatures and problems associated with high processing temperatures. As one non-limiting example, the synthetic wax can be soluble in, or compatible with, cyclopentasiloxane at a temperature of less than or equal to 100° C., 95° C., 90° C., or 85° C. at a concentration of 5 wt % in the cyclopentasiloxane solvent.

Some non-limiting examples of waxes can be or can include long chain alkanes (e.g. paraffins/iosparaffins), long chain alcohols, alkyl methicones, polyethylenes, alkyldimethylsilyl polypropylsilsesquioxanes, the like, or combinations thereof. In some specific examples, the synthetic wax can be or include $C_{18}$-$C_{70}$ alkanes (e.g. $C_{18}$-$C_{70}$ paraffins/isoparaffins), or the like. In yet other specific examples, the synthetic wax can be or include $C_{20}$-$C_{40}$ alcohols, or the like. In further specific examples, the synthetic wax can be or include $C_{30}$-$C_{45}$ alkyl methicones, or the like. In additional specific examples, the synthetic wax can be or include $C_{30}$-$C_{45}$ olefins, or the like. In still other specific examples, the synthetic wax can be or include $C_{30}$-$C_{45}$ alkyldimethylsilyl polypropylsilsesquioxanes, or the like. Any suitable combination of the specific synthetic waxes listed above can also be used. Where the synthetic wax includes a long chain alcohol, the synthetic wax can have a hydroxyl number of from about 80 milligrams (mg) potassium hydroxide (KOH)/gram (g) to about 150 mg KOH/g. In some other examples, where the synthetic wax includes a long chain alcohol, the synthetic wax can have a hydroxyl number of from about 100 mg KOH/g to about 140 mg KOH/g, or from about 110 mg KOH/g to about 130 mg KOH/g.

The synthetic wax can have a variety of sizes and/or or size distributions. In some specific examples, the synthetic wax can have a weight average molecular weight (Mw) of from about 100 g/mol to about 2000 g/mol. In some additional examples, the synthetic wax can have an Mw of from about 200 g/mol to about 1200 g/mol. In yet other examples, the synthetic wax can have an Mw of from about 250 g/mol to about 1000 g/mol.

The synthetic wax can be either a linear or branched wax, as desired. In some examples, the synthetic wax can be a linear, or substantially linear, synthetic wax. Specifically, in some examples, the synthetic wax can have less than 20%, less than 10%, less than 5%, or less than 2% branching. In yet other examples, the synthetic wax can be a branched wax. Where the synthetic wax is branched, the wax can typically have at least 1%, at least 2%, at least 5%, at least 10%, or at least 15% branching.

Further, in some examples, the synthetic wax can have a viscosity of from about 0.1 centipoise (cps) to about 20 cps at a temperature of 99° C. In other examples, the synthetic wax can have a viscosity of from about 2 cps to about 10 cps at a temperature of 99° C. In yet other examples, the synthetic wax can have a viscosity of from about 0.2 cps to about 4 cps, or from about 0.5 cps to about 5 cps at a temperature of 99° C. In still additional examples, the synthetic wax can have a viscosity of from about 3 cps to about 5 cps, or from about 4 cps to about 8 cps at a temperature of 99° C. The viscosity can be measured using ASTM D88, ASTM D2161, modified versions thereof or other suitable methods for measuring viscosity.

In additional examples, the synthetic wax can have a needle penetration value of from about 8 decimillimeters (dmm) to about 30 dmm at 25° C. In yet other examples, the synthetic wax can have a needle penetration value of from about 10 dmm or 15 dmm to about 25 dmm at 25° C., or from about 18 dmm to about 22 dmm at 25° C. As will be recognized by one skilled in the art, needle penetration tests are performed on petroleum products and other waxy products to determine consistency and shear stability for design, quality control, and identification purposes. ASTM D1321 describes a specific example of how this test can be performed, though some minor modifications may be advisable when testing some materials. As one non-limiting example, the sample can be heated to a predetermined temperature (e.g. a predetermined temperature above its congealing point), subsequently cooled, and placed in a water bath at the test temperature for predetermined time period (e.g. 1 hour). The sample can be positioned under a pentrometer needle, which is released and penetrates into the sample. Specifically, a needle having truncated cone tip can be applied at a load of about 100 grams for about 5 seconds. The depth of penetration of the needle into the sample is typically measured in tenths of a millimeter by the penetrometer and is reported as the needle penetration value.

Where the synthetic wax is employed as a secondary structurant, the synthetic wax can be present in the antiperspirant composition in a variety of amounts. In some examples, the synthetic wax can be present in an amount from about 0.5 wt % to about 3 wt %. In yet other examples, the synthetic wax can be present in an amount from about 1 wt % to about 2.5 wt %, or from about 1.5 wt % to about 2 wt %.

It is noted that, in some examples, where the synthetic wax is employed as a secondary structurant, the synthetic wax alone may not provide the antiperspirant composition with a sufficiently high melting point to prevent syneresis of some of the liquid components of the formulation. In such cases, it can be beneficial to include a melting point additive in the antiperspirant stick composition. In some examples, the melting point additive can also act as a lubricant, emollient, and/or solvent in the formulation. Thus, the melting point additive can be suitable to provide or facilitate (or at least not adversely affect) a desired or adequate texture and/or slip for the stick composition while maintaining an overall melting point of the stick composition at a level that would be suitable for typical storage and transportation temperatures. The melting point additive can typically be any suitable additive that, when in combination with the other ingredients of the formulation, provides the composition with a melting point greater than or equal to 40° C. 42° C., 45° C., 48° C., or above without adversely affecting the texture, slip, and/or other desired properties of the stick composition. In some examples, the melting point additive does not actually increase the melting point of the stick composition as compared to the melting point of the stick composition without the melting point additive. Where this is the case, the melting point additive can be a desired lubricant, emollient, and/or solvent, that does not lower the overall melting point of the stick composition below 40° C., 42° C. 45° C., or 48° C. for example. Thus, the melting point additive can provide the antiperspirant stick composition with increased thermal stability at typical transportation and storage temperatures. Accordingly, in some examples, the melting point additive can be present at a weight ratio with the synthetic wax to provide the antiperspirant stick composition with a melting point greater than or equal to 40° C., 42° C., 45° C., 48° C., or above.

A variety of melting point additives can be used. Non-limiting examples can include $C_{12}$-$C_{15}$ alkyl benzoates, mineral oil, dimethicone, the like, or combinations thereof. In some specific examples, the melting point additive can include $C_{12}$-$C_{15}$ alkyl benzoates. In yet other examples, the melting point additive can include mineral oil. Where this is the case, the mineral oil can typically have a Saybolt color (ASTM D156) of at least 30 and/or an ambient viscosity of from about 15 centistokes to about 100 centistokes (cst). In some examples, the melting point additive can include dimethicone. Where this is the case, the dimethicone can typically have an ambient viscosity of from about 50 cst to about 1000 cst. In yet other examples, the dimethicone can have an ambient viscosity of from about 100 cst to about 400 cst.

The melting point additive can be present in the composition in an amount that provides the composition with the desired thermal stability. In some specific examples, the melting point additive can be present in the antiperspirant stick composition in an amount from about 5 wt % to about 20 wt %. In yet other examples, the melting point additive can be present in the antiperspirant stick composition in an amount from about 7 wt % to about 15 wt %, or from about 8 wt % to about 12 wt %. In yet other examples, the melting point additive can be present at a predetermined weight ratio to the synthetic wax. For example, in some cases, the melting point additive and the synthetic wax can be present at a weight ratio of from about 1:1 to about 15:1 melting point additive to synthetic wax. In yet other examples, the melting point additive and the synthetic wax can be present at a weight ratio of from about 2:1 to about 10:1, from about 4:1 to about 8:1, or from about 5:1 to about 7:1 melting point additive to synthetic wax.

In some examples, the antiperspirant stick composition can also include a lubricant. In some examples, the lubricant can be or include a volatile silicone. Non-limiting examples of lubricants can include cyclopentasiloxane, cyclohexasiloxane, dimethylpolysiloxane, methylphenylpolysiloxane, hexamethyldisiloxane, octamethyltrisiloxane, decamethyltetrasiloxane, or combinations thereof.

The lubricant can be present in the antiperspirant stick composition in a variety of amounts. In some examples, the lubricant can be present in the antiperspirant stick composition in an amount from about 20 wt % to about 40 wt %. In yet other examples, the lubricant can be present in the antiperspirant stick composition in an amount from about 25 wt % to about 35 wt %.

In some additional examples, the antiperspirant can include an emollient to help provide a soothing effect on the skin. A variety of suitable emollients are known in the art and can be used in the present formulation. Non-limiting examples can include $C_{12}$-$C_{15}$ alkyl benzoate, PPG-13 butyl ether, PPG-14 butyl ether, PPG-9 butyl ether, PPG-10 butanediol, PPG-15 stearyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxyl alkyls, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide, the like, or combinations thereof.

When used, emollients can be included in the composition in a variety of amounts. In some specific examples, the emollient can be included in the antiperspirant stick composition in an amount from about 0.5 wt % to about 35 wt %. In yet other examples, the emollient can be present in an amount from about 1 wt % to about 30 wt %, from about 7 wt % to about 15 wt %, from about 10 wt %, to about 25 wt %, from about 12 wt % to about 22 wt %, or from about 5 wt % to about 18 wt %.

In some examples, the antiperspirant stick composition can also include a fragrance. Any suitable fragrance can be used in the antiperspirant stick composition. Examples of fragrance compounds of the ester type are benzyl acetate, phenoxyethyl isobutyrate, p-tert-butyl cyclohexyl acetate, linalyl acetate, dimethyl benzyl carbinyl acetate (DMBCA), phenylethyl acetate, benzyl acetate, ethyl methyl phenyl glycinate, allyl cyclohexyl propionate, styrallyl propionate, benzyl salicylate, cyclohexyl salicylate, floramat, melusat and jasmecyclate. Examples of fragrance compounds of the ether type are benzyl ethyl ethers and ambroxan. Examples of fragrance compounds of the aldehyde type are the linear alkanals having 8-18 C atoms, citral, citronellal, citronellyl oxyacetaldehyde, cyclamen aldehyde, lilial and bourgeonal. Examples of fragrance compounds of the ketone type are iononeS, alpha-isomethyl ionone and methyl cedryl ketone. Examples of fragrance compounds of the alcohol type are anethol, citronellol, eugenol, geraniol, linalool, phenylethyl alcohol and terpineol. Examples of fragrance compounds of the terpene type are limonene and pinene. Additional examples of fragrance compounds are pine oil, citrus oil, jasmine oil, patchouli oil, rose oil, ylang-ylang oil, muscatel sage oil, chamomile oil, clove oil, mint oil, cinnamon leaf oil, lime blossom oil, juniper berry oil, vetiver oil, olibanum oil, *galbanum* oil, laudanum oil, orange blossom oil, neroli oil, orange peel oil and sandalwood oil, also the essential oils such as *angelica* root oil, aniseed oil, *arnica* flower oil, basil oil, bay oil, bergamot oil, champaca flower oil, noble fir oil, noble fir cone oil, elemi oil, *eucalyptus* oil, fennel oil, spruce needle oil, geranium oil, gingergrass oil, guaiac wood oil, gurjun balsam oil, helichrysum oil, hon-sho oil, ginger oil, iris oil, cajeput oil, calamus oil, chamomile oil, camphor oil, *cananga* oil, cardamom oil, *cassia* oil, pine needle oil, copaiba balsam oil, coriander oil, spearmint oil, caraway oil, cumin oil, lavender oil, lemongrass oil, lime oil, mandarin oil, melissa oil, musk seed oil, myrrh oil, clove oil, niaouli oil, orange oil, *origanum* oil, palmarosa oil, patchouli oil, Peru balsam oil, petitgrain oil, pepper oil, peppermint oil, pimento oil, pine oil, rose oil, rosemary oil, sandalwood oil, celery oil, spike lavender oil, star anise oil, turpentine oil, *thuja* oil, thyme oil, *verbena* oil, juniper berry oil, wormwood oil, wintergreen oil, hyssop oil, cinnamon oil, citronella oil, lemon oil and cypress oil. Yet additional examples of fragrance compounds are ambrettolide, α-amylcinnamaldehyde, anethol, anisaldehyde, anisic alcohol, anisol, methyl anthranilate, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptine carboxylate, heptaldehyde, hydroquinone dimethyl ether, hydroxycinnamaldehyde, hydroxycinnamic alcohol, indole, irone, isoeugenol, isoeugenol methyl ether, isosafrole, jasmone, camphor, carvacrol, carvone, p-cresol methyl ether, coumarin, p-methoxyacetophenone, methyl-n-amyl ketone, methyl methyl anthranilate, p-methyl acetophenone, methyl chavicol, p-methyl quinoline, methyl-β-naphthyl ketone, methyl-n-nonyl acetaldehyde, methyl-n-nonyl ketone, muscone, β-naphthol ethyl ether, β-naphthol methyl ether, nerol, nitrobenzene, n-nonyl aldehyde, nonyl alcohol, n-octyl aldehyde, p-oxyacetophenone, pentadecanolide, β-phenylethyl alcohol, phenyl acetaldehyde dimethyl acetal, phenyl acetic acid, pulegone, safrole, isoamyl salicylate, methyl salicylate, hexyl salicylate, cyclohexyl salicylate, santalol, skatole, terpineol, thymene, thymol, gamma-undecalactone, vanillin, veratrum aldehyde, cinnamaldehyde, cinnamyl alcohol, cinnamic acid, ethyl cinnamate, and benzyl cinnamate. Further (more highly volatile) fragrances are alkyl isothiocyanates (alkyl mustard oils), butanedione, limonene, linalool, linalyl acetate and propionate, methyl-n-heptenone, phellandrene, phenylacetaldehyde, terpinyl acetate, citral and citronellal. Suitable perfume oils can also contain natural fragrance mixtures, such as are obtainable from plant or animal sources, for example pine, citrus, jasmine, rose, lily or ylang-ylang oil. Low-volatility essential oils, which are mostly used as aroma components, are also suitable as perfume oils, for example sage oil, chamomile oil, melissa oil, mint oil, cinnamon leaf oil, lime blossom oil, juniper berry oil, vetiver oil, olibanum oil, *galbanum* oil, laudanum oil, clove oil, iso-eugenol, thyme oil, bergamot oil, geranium oil and rose oil. Any suitable combination of these, or other, fragrance compounds and/or perfume oils can likewise be used.

In some examples, the antiperspirant stick composition can also include a sweat-sequestering agent. As previously noted, the human body includes both eccrine sweat glands and apocrine sweat glands, both of which are present in the underarm area. Eccrine sweat glands produce a clear, aqueous electrolye composition, whereas apocrine sweat glands produce an oily composition. These various types of sweat, in combination with various components of antiperspirant compositions, can enhance the discoloration of textiles that come into contact with antiperspirant compositions. Accordingly, a variety of sweat-sequestering agents can be employed in the present composition. Sweat-sequestering agents can include hydrophobic surfactants, hydrophilic surfactants, the like, or a combination thereof.

It is noted that the antiperspirant stick composition can already include a variety of hydrophobic components as primary and secondary structurants that can help sequester apocrine sweat. Thus, in some examples, the sweat-sequestering agent can include a hydrophilic surfactant. Hydrophilic surfactants can help combat sweat-induced fabric discoloration or staining resulting from eccrine sweat. The hydrophilic surfactant can have a hydrophilic-lipophilic balance (HLB) value greater than or equal to 10. In some examples, the hydrophilic surfactant can have an HLB value greater than or equal to 12, greater than or equal to 14, or greater than or equal to 16.

Non-limiting examples of hydrophilic surfactants can include Polyethylene glycol (400) monooleate, Didodecyldimethylammoniumchloride, Polyethylene glycol (200) monolaurate, Polyethylene glycol (400) dilaurate, Polyethylene glycol (600) dioleate, Polyoxyethylene (4) sorbitan monostearate, Polyoxyethylene (5) sorbitan monooleate, Polyoxyethylene (40) sorbitol hexaoleate, Polyoxyethylene glycol (600) distearate, Polyoxyethylene (20) sorbitan tristearate, Sucrose monostearate, Sucrose monooleate, Polyethylene glycol (400) monooleate, Polyethylene glycol (350) monostearate, Polyethylene glycol (400) monotalleate, Polyoxyethylene glycol (7) monostearate, Polyoxyethylene glycol (8) monooleate, Polyoxyethylene (20) sorbitan trioleate, Polyoxyethylene (6) tridecyl alcohol, Polyethylene glycol (400) monostearate, Polyoxyethylene (9) monostearate, Sucrose monooleate, Sucrose monostearate, Polyoxyethylene (50) sorbitol hexaoleate, Sucrose monotalleate, Sucrose stearate palmitate, Polyoxyethylene glycol (400) monoricinoleate, Sucrose monomyristeate, Sucrose monopalmitate, PEG-10 Soy Sterol (e.g., GENEROL® 122 E 10), Triethanolamine oleate, Nonylphenol (ethoxylated) with 8 Mol EO, Sucrose monomyristeate, Sucrose monolaurate, Polyoxyethylene (10) oleyl alcohol, polyoxyethylene (10) oleyl ether, Polyoxyethylene (10) stearyl alcohol, polyoxyethylene (10) stearyl ether, Polyoxyethylene (10) stearylcetyl ether, Polyoxyethylene (8) tridecyl alcohol, Polyoxyethylene glycol (400) monolaurate, Sucrose monococoate, Polyoxyethylene (10) cetylether, Glycerol monostearate (ethoxylated) (20 Mol EO), EUMULGIN® O 10, EUMULGIN® 286, EUMULGIN® B 1 (Ceteareth-12), $C_{12}$-fatty amines (ethoxylated) (5 Mol EO), Nonylphenol (ethoxylated) (9.5 Mol EO), Polyethylene glycol (600) monostearate, Polyoxyethylene (16) tallow oil, Polyoxyethylene (4) sorbitan monolaurate, Nonylphenol (ethoxylated) (10.5 Mol EO), Polyethylene glycol (600) monooleate, Polyoxyethylene (10) tridecyl alcohol, Polyethylene glycol (660) monotallowate, Polyethylene glycol (1500) monostearate, Polyoxyethylene glycol (1500) dioleate, Polyethylene glycol (400) monococoate, Polyoxyethylene (9) monolaurate, EUMULGIN® HRE 40 (Ricinus oil, ethoxylated and hydroxylated with 40 Mol EO), Polyoxyethylene (12) lauryl ether, Polyoxyethylene (12) tridecyl alcohol, Polyoxyethylene (15) stearyl alcohol, Polyoxyethylene (15) stearylcetyl ether, Mixture of $C_{12}$-$C_{15}$ fatty alcohols with 12 Mol EO, Polyoxyethylene (12) lauryl alcohol, Polyoxyethylene glycol (600) monolaurate, Sorbitan monostearate (ethoxylated with 20 Mol EO) (e.g., EUMULGIN® SMS 20), Sorbitan monooleate (ethoxylated with 20 Mol EO) (e.g., EUMULGIN® SMO 20), PEG-20 Glyceryl stearate (e.g., CUTINA® E 24), PEG-40 Castor Oil (e.g., EUMULGIN® RO 40), Decyl glucoside (e.g. ORAMIX™ NS 10), Dodecyl glucoside (e.g. PLANTAREN® APG 600), Dodecyl trimethyl ammonium chloride, Nonylphenol (ethoxyalted with 15 Mol EO), Polyethylene glycol (1000) monostearate, Polyoxyethylene (600) monooleate, EUMULGIN® HRE 60 (Ricinus oil, ethoxylated and hydrated with 60 Mol EO), $C_{12}$-fatty amines (polyoxyethylated with 12 Mol EO), Polyoxyethylene (20) oleyl alcohol, polyoxyethylene (20) oleylether, Polyoxyethylene (20) stearylcetylether (e.g. EUMULGIN® B 2 (Ceteareth-20)), Polyoxyethylene (20) stearyl alcohol, Polyoxyethylene glycol (1000)monostearate, Polyoxyethylene (20) sorbitan monopalmitate, Polyoxyethylene (20) cetyl ether, Disodium triethanolamine distearyl heptaglycol ether sulfosuccinate, Nonylphenol (ethoxylated with 20 Mol EO), Polyoxyethylene (25) propylene glycol stearate, Polyoxyethylene (30) monostearate, Polyoxyethylene (40) monostearate, Polyoxyethylene (20) sorbitan monolaureate (e.g., EUMULGIN® SML 20), Polyoxyethylene (20) sorbitol, $C_{18}$ fatty amines (polyoxyethylated with 5 Mol EO), Polyoxyethylene (23) lauryl alcohol, Ceteareth-30 (e.g. EUMULGIN® B 3), Octyl glucoside (e.g. TRITON™ CG 110), Polyoxyethylene (30) glyceryl monolaurate, Nonylphenol (ethoxylated with 30 Mol EO), Polyoxyethylene (40) stearyl alcohol, the like, or combinations thereof.

In some specific examples, the hydrophilic surfactant can be selected based on compatibility with cationic active agents. In some examples, the hydrophilic surfactant can be a non-ionic surfactant. In some additional examples, the hydrophilic surfactant can be an alkoxylated surfactant, such as an ethoxylated surfactant or a propoxylated surfactant, for example. In some specific examples, the hydrophilic surfactant can have a molecular formula of R—(OA)$_n$-OH, where R represents a $C_{12}$-$C_{24}$ alkyl group, OA represents an ethylene oxide or propylene oxide group, and n represents an integer from 10 to 50, or from 20 to 40. In some specific examples, R can be a $C_{14}$-$C_{20}$ alkyl group, or a $C_{16}$-$C_{18}$ alkyl group. In some additional examples, n can be an integer from 22 to 38, or 25 to 35.

In some examples, the hydrophilic surfactant can have a melting point of greater than or equal to 35° C. In yet other examples, the hydrophilic surfactant can have a melting point of greater than or equal to 30° C., or greater than or equal to 40° C. In some examples, introducing a surfactant with a relatively high melting temperature can add additional thermal stability to the antiperspirant stick composition.

The hydrophilic surfactant can be present in the antiperspirant composition in a variety of amounts. Generally, the hydrophilic surfactant can be present in an amount sufficient to reduce or minimize perspiration-induced discoloration of fabric in contact with the composition. In some specific examples, the hydrophilic surfactant can be present in the antiperspirant stick composition in an amount from about 2 wt % to about 10 wt %. In yet other examples, the hydrophilic surfactant can be present in the antiperspirant stick composition in an amount from about 3 wt % to about 8 wt %, or from about 4 wt % to about 6 wt %.

However, it is noted that in some cases where a hydrophilic surfactant is included in the antiperspirant composition, the hydrophilic surfactant can have a negative impact on the texture of the antiperspirant stick composition. Specifically, when the composition comes into contact with water or other aqueous based compositions, the antiperspirant stick composition can develop a plastic-like or glazed feel (i.e. "egg-shell" effect). This can adversely affect the delivery of the antiperspirant stick composition and antiperspirant active agent to the skin. As such, in some examples, a plasticizer can be added to the antiperspirant stick composition in an amount to minimize hardening of the composition due to contact with an aqueous composition. In some specific examples, the plasticizer can be present in the antiperspirant stick composition in an amount from about 0.5 wt % to about 5 wt %. In yet other examples, the plasticizer can be present in the antiperspirant stick composition in an amount from about 0.75 wt % to about 4 wt %, or from about 1 wt % to about 3 wt %.

In some examples, the hydrophilic surfactant and the plasticizer can be present at a predetermined weight ratio. For example, in some cases, the hydrophilic surfactant and the plasticizer can be present at a weight ratio of from 1:1 to 6:1 hydrophilic surfactant to plasticizer. In yet other examples, the hydrophilic surfactant and the plasticizer can be present at a weight ratio of from 2:1 to 3:1 hydrophilic surfactant to plasticizer.

A variety of plasticizers can be used. Non-limiting examples can include propylene carbonate, propylene glycol, glycerol carbonate, glycerin, butylene carbonate, butylene glycol, the like, or combinations thereof.

The antiperspirant stick compositions can also include an effective amount of an antiperspirant active agent. As previously mentioned, in some examples, the antiperspirant stick composition can include relatively small amounts of, or be substantially free of, highly discoloring agents, such as hydrogenated oils, petrolatum, and combinations thereof. In yet other examples, the antiperspirant stick compositions can include a sweat-sequestering agent to help reduce or minimize sweat-induced discoloration of textile materials.

Accordingly, due to modifications to the formulation itself to reduce the staining properties of the formulation, or by including a sweat-sequestering agent in the formulation to minimize sweat-induced fabric staining, or both, the present antiperspirant stick compositions can include effective amounts of antiperspirant active agents and still reduce or minimize the fabric-staining properties of the composition.

An effective amount of an antiperspirant active agent can be selected in view of the particular antiperspirant active agent employed. In some examples, an effective amount of the antiperspirant active agent can be an amount greater than or equal to 12 wt %, 14 wt %, or 16 wt %. In some specific examples, the antiperspirant active agent can be present in the antiperspirant stick composition in an amount from about 14 wt % to about 22 wt %. In yet other examples, the antiperspirant active agent can be present in the antiperspirant stick composition in an amount from about 16 wt % to about 20 wt %, or from about 18 wt % to about 24 wt %.

In yet other examples, the antiperspirant active agent and the primary structurant, such as a fatty alcohol or fatty acid, for example, can be present at a weight ratio of from about 1:2 to about 2:1 antiperspirant active agent to primary structurant. In yet other examples, the antiperspirant active agent and the primary structurant can be present at a weight ratio of from about 1:1.5 to about 1.5:1, or from about 1:1.2 to about 1.2:1 antiperspirant active agent to primary structurant. In some specific examples, the primary structurant can be a fatty alcohol. Where this is the case, the antiperspirant active agent and total fatty alcohols (i.e. primary structurant and any additional fatty alcohols incorporated in the formulation) can be present at a weight ratio from about 1:2 to about 2:1, from about 1:1.5 to about 1.5:1, or from about 1:1.2 to about 1.2:1 antiperspirant active agent to fatty alcohol.

In yet other examples, the antiperspirant active agent and the lubricant can be present at a predetermined weight ratio. In some examples, the antiperspirant active agent can be present with the lubricant at a weight ratio of from about 1:0.75 to about 1:2.5 antiperspirant active agent to lubricant. In yet other examples, the antiperspirant active agent that the lubricant can be present at a weight ratio of from about 1:1 to about 1:2.2, or from about 1:1.2 to about 1:2 antiperspirant active agent to lubricant.

A variety of antiperspirant active agents can be used in the present antiperspirant stick compositions. Non-limiting examples can include aluminum chlorohydrate, aluminum chloride, aluminum hydroxide, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate polyethylene glycol, aluminum sesquichlorohydrate propylene glycol, aluminum-zirconium octachlorohydrate, aluminum-zirconium octachlorohydrex glycine, aluminum-zirconium pentachlorohydrate, aluminum-zirconium pentachlorohydrex glycine, aluminum-zirconium tetrachlorohydrate, aluminum-zirconium tetrachlorohydrex glycine, aluminum-zirconium trichlorohydrate, aluminum-zirconium trichlorohydrex glycine, potassium aluminum sulfate, aluminum undecylenoyl collagen amino acid, sodium aluminum lactate, aluminum sulfate, sodium aluminum chlorohydroxylactate, aluminum bromohydrate, aluminum chlorohydroxyallantoinate, zinc chloride, zinc sulfocarbolate, zinc sulfate, zirconium chlorohydrate, the like, or combinations thereof.

In some examples, the antiperspirant stick compositions can also include a number of other suitable ingredients. Non-limiting examples can include bulking agents (e.g. talc, silica, clay, etc.), antioxidants, antimicrobials (e.g. antibacterials, antifungals, etc.), other suitable ingredients, or combinations thereof.

The present disclosure also describes a number of methods associated with the antiperspirant stick compositions. A number of specific, but non-limiting, examples are provided below. For example, methods of minimizing, controlling, reducing, or substantially eliminating fabric-staining properties of an antiperspirant stick composition can include adding a synthetic wax to the composition, adding a melting point additive to the composition at a weight ratio to the synthetic wax to provide the composition with a melting point greater than or equal to 40° C., adding an effective amount of an antiperspirant active agent to the composition, and limiting an amount of hydrogenated oils, petrolatum, 12-hydroxystearic acid, polyethylenes having a melting point greater than or equal to 60° C., and combinations thereof in the composition to less than 2 wt %. The synthetic wax can have a melting point of less than or equal to 90° C.

In other examples, methods of controlling, minimizing, reducing, or substantially eliminating fabric-staining resulting from contact of a fabric with an antiperspirant composition can include limiting an amount of hydrogenated oils, petrolatum, 12-hydroxystearic acid, polyethylenes having a melting point greater than or equal to 60° C., and combinations thereof in the composition to less than 2 wt %, structuring the composition with a synthetic wax having a melting point of less than or equal to 90° C., and adding a melting point additive at a weight ratio to the synthetic wax to provide the composition with a melting point greater than or equal to 40° C. Additionally, the composition can include an effective amount of an antiperspirant active agent.

In yet other examples, methods of minimizing, controlling, reducing, or substantially eliminating the fabric-staining properties of an antiperspirant stick composition can include adding an amount of a synthetic wax to the composition, adding a melting point additive to the composition in an amount sufficient to provide the composition with a melting point greater than or equal to 40° C., adding an amount of a fatty alcohol to the composition, and adding an effective amount of an antiperspirant active agent to the composition. The fatty alcohol and the antiperspirant active agent can be present at a weight ratio of from 2:1 to 1:2. Additionally, the synthetic wax can have a melting point less than or equal to 90° C.

In still other examples, methods of substantially eliminating, controlling, reducing, or otherwise minimizing fabric-staining resulting from contact of a fabric with an antiperspirant stick composition can include structuring the antiperspirant stick composition with a synthetic wax and a fatty alcohol, adding a melting point additive to the composition in an amount sufficient to provide the composition with a melting point greater than or equal to 40° C., and incorporating or including an effective amount of an antiperspirant active agent in the composition. The fatty alcohol and the antiperspirant active agent can be present at a weight ratio of from 2:1 to 1:2. Additionally, the synthetic wax can have a melting point of less than or equal to 90° C.

In some examples, methods of controlling reducing, substantially eliminating, or otherwise minimizing perspiration-induced discoloration of fabric due to contact with an antiperspirant stick composition can include adding a synthetic wax to the composition, adding a fatty alcohol to the composition, adding a hydrophilic surfactant to the composition in an amount sufficient to minimize perspiration-induced discoloration of fabric in contact with the composition, adding a plasticizer to the composition in an amount to minimize hardening of the composition due to contact with an aqueous composition, and adding an effective amount of an antiperspirant active agent to the composition. The fatty alcohol and the antiperspirant active agent can be present at a weight ratio of from 2:1 to 1:2. Further, the hydrophilic surfactant can have an HLB value greater than 10.

In other examples, methods of controlling, or reducing, or minimizing, or substantially eliminating perspiration-induced discoloration of fabric resulting from contact of a fabric with an antiperspirant stick composition can include incorporating or including a hydrophilic surfactant in the composition in an amount sufficient to minimize perspiration-induced discoloration of the fabric due to contact with the composition, incorporating or including a plasticizer in the composition in an amount to minimize hardening of the composition due to contact with an aqueous composition, and structuring the composition with a synthetic wax and a fatty alcohol. The composition can include an effective amount of an antiperspirant active agent such that the fatty alcohol and the antiperspirant active agent are present at a weight ratio of from 2:1 to 1:2. Additionally, the hydrophilic surfactant can have an HLB value greater than 10.

In yet other examples, methods of substantially eliminating, or at least minimizing or reducing, or controlling perspiration-induced discoloration of fabric due to contact with an antiperspirant stick composition can include adding a synthetic wax to the composition, adding a hydrophilic surfactant to the composition in an amount sufficient to minimize perspiration-induced discoloration of the fabric due to contact with the composition, adding a plasticizer to the composition in an amount sufficient to minimize hardening of the composition due to contact with an aqueous composition, and adding an effective amount of an antiperspirant active agent to the composition. The synthetic wax can have a viscosity of from about 0.1 centipoise (cps) to about 20 cps at a temperature of 99° C. The hydrophilic surfactant can have an HLB value greater than 10.

In still other examples, methods of controlling, reducing, minimizing, or substantially eliminating perspiration-induced discoloration of fabric resulting from contact of a fabric with an antiperspirant stick composition can include incorporating or including a hydrophilic surfactant in the composition in an amount sufficient to minimize perspiration-induced discoloration of the fabric due to contact with the composition, incorporating or including a plasticizer in the composition in an amount to minimize hardening of the composition due to contact with an aqueous composition, and structuring the composition with a synthetic wax having a viscosity of from about 0.1 centipoise (cps) to about 20 cps at a temperature of 99° C. The composition can include an effective amount of an antiperspirant active agent. Additionally, the hydrophilic surfactant can have an HLB value greater than 10.

It is noted that with each of these non-limiting methods, the antiperspirant stick compositions can be formulated in a variety of ways as described above. It is further noted that structuring the antiperspirant stick composition with a synthetic wax, or a synthetic wax in combination with a fatty alcohol, can, in some cases, provide a formulation with reduced or minimized fabric-staining or discoloring properties. Thus, in some examples, mere application of the antiperspirant stick composition to a fabric material can be minimally staining or discoloring to the fabric material. In many cases, this can permit the use of effective amounts of an antiperspirant active agent while maintaining reduced or minimized fabric-staining potential.

In other examples, the addition of a sweat-sequestering agent, such as a hydrophobic surfactant, a hydrophilic surfactant, or the like can provide an antiperspirant stick composition that can reduce or minimize perspiration-induced discoloration of fabric materials. For example, in some cases, the antiperspirant stick composition can already include a variety of hydrophobic components that can help sequester apocrine sweat. Thus, inclusion of a hydrophilic surfactant in the antiperspirant stick composition can, in some cases, also help sequester eccrine sweat. In some examples, the hydrophilic surfactant can help prevent eccrine sweat from contacting the fabric material. In other examples, the hydrophilic surfactant can help remove eccrine sweat and/or other components of the antiperspirant stick composition from the fabric material.

It is noted that antiperspirant compositions can cause discoloration of a variety of fabrics, such as cotton, polyesters, polyamides (e.g. nylon), linen, etc. Thus, when discussing discoloration of fabrics, any type of fabric that comes into contact with an antiperspirant stick composition is considered to be within the present scope. However, in some examples, the fabric can be or include cotton. In yet other examples, the fabric can be or include polyester. In still other examples, the fabric can be or include nylon. In other examples, the fabric can be or include linen.

Further, when discussing the discoloration of fabrics, discoloration can be measured using a color measurement instrument, such as a colorimeter. For example, color measurements can be quantified using the L*a*b* color space as defined by the Commission Internationale de l'Eclairage (CIE). L*, a*, and b* values have been defined in specific color coordinate areas and can be used to quantify specific types of color changes. Specifically, L* values indicate lightness vs darkness of a sample (+=lighter, −=darker), a* values indicate the degree of red vs green in a sample (+=redder, −=greener), and b* values indicate the degree of yellow vs blue in a sample (+=yellower, −=bluer). Thus, any one of these values, or other defined color values, can be used to measure discoloration or staining of fabrics. In some specific examples, b* values (e.g. delta b* values) can be used to measure the discoloration of fabrics. In yet other examples, a* values (e.g. delta a* values) can be used to measure the discoloration of fabrics. In still other examples, L* values (e.g. delta L* values) can be used to measure the discoloration of fabrics. Thus, discoloration of fabrics, or fabric-staining, can be measured as a change in b* value, for example, of an area of the fabric that has contacted the antiperspirant stick composition as compared to a control area of the fabric that has not contacted the antiperspirant stick composition.

It is noted that when discussing the antiperspirant stick composition, the method of minimizing fabric-staining resulting from contact of a fabric with an antiperspirant composition, the method of minimizing perspiration-induced discoloration of fabric resulting from contact of a fabric with an antiperspirant stick composition, and other methods described herein, each of these discussions can be considered applicable to each of these examples, whether or not they are explicitly discussed in the context of that example. Thus, for example, in discussing details about the antiperspirant stick composition per se, such discussion also refers to the various methods described herein, and vice versa.

EXAMPLES

Example 1—In Vitro Wash Study

A synthetic eccrine sweat solution was prepared as presented in Table 1 below.

TABLE 1

Eccrine Sweat Solution

| Component | Molecular Weight (gram/mol) | mg/dL deionized water |
|---|---|---|
| $Na_2SO_4$ (10 H2O) | 322.2 | 269 |
| $NaH_2PO_4$ (1 H2O) | 137.99 | 36.5 |
| $MgCl_2$ (6 H2O) | 293.3 | 130 |
| $CaCl_2$ (6 H2O) | 219.08 | 110 |
| KCl | 74.55 | 382 |
| NaCl | 58.4 | 4965 |
| Urea | 60 | 320 |
| Glycine | 75 | 54 |
| $NH_4OH$ (25%) | 35 | 400 |
| Glucose | 180 | 20 |
| Lactic Acid (85%) | 90 | 315 | pH = 5.1-5.3 adjusted by lactic acid 0.7 g antiperspirant and 1 ml synthetic sweat solution was mixed to be homogeneous and then applied to a cotton t-shirt. Stains were aged for one hour and then washed in a standard washer at medium temperature. The t-shirts were combined with 6 lbs of ballast (pillow cases) to simulate a normal wash load. It is noted that 100% cotton t-shirts were selected because cotton has been shown to have very high staining potential for yellow antiperspirant stains. The laundry detergent used was PUREX® Free n Clear laundry detergent. After the wash cycle, the wash load was dried in an electric drier for 50 minutes on the cotton setting. The staining and washing procedure was repeated for a total of 10 cycles. After the 10 stain/wash cycles, measurements were performed using a Gardner Colorimeter to determine the b* value of the stained areas of the cotton t-shirts as compared to a blank (untreated) area of the same t-shirt. The difference in b* values between the sample regions and the blank region of each t-shirt were used to generate delta b* values. The results are presented in Table 2 below. All delta b* values are based on an average of four replicates.

TABLE 2

Wash Study Results

| APDO Sample | b* 1 | b* 2 | b* 3 | b* 4 | Avg b* | Delta b* |
|---|---|---|---|---|---|---|
| Blank | 1.44 | 1.47 | 1.48 | 1.48 | 1.4675 | |
| OS pure sport | 4.35 | 4.42 | 4.52 | 4.36 | 4.4125 | 2.945 |
| OS swagger | 4.27 | 3.76 | 4.16 | 3.86 | 4.0125 | 2.545 |
| OS fiji | 4.13 | 4.3 | 4.2 | 4.42 | 4.2625 | 2.795 |
| OS wolfthorn | 5.21 | 5.43 | 5.24 | 5.47 | 5.3375 | 3.87 |
| GILLETTE ® | 4.37 | 4.13 | 4.42 | 4.26 | 4.295 | 2.8275 |
| Blank | 1.52 | 1.62 | 1.59 | 1.62 | 1.5875 | |
| DEGREE ® | 3.28 | 3.32 | 3.29 | 3.41 | 3.325 | 1.7375 |
| DEGREE ® adv | 3.11 | 3.16 | 3.61 | 3.51 | 3.3475 | 1.76 |
| DEGREE ® uc | 4.16 | 3.68 | 3.72 | 3.66 | 3.805 | 2.2175 |
| AXE ® phoenix | 3.57 | 3.27 | 3.2 | 3.29 | 3.3325 | 1.745 |
| AXE ® gold | 3.12 | 3.66 | 3.59 | 3.16 | 3.3825 | 1.795 |
| Blank | 1.77 | 1.87 | 1.76 | 1.85 | 1.8125 | |
| DOVE ® | 4.34 | 4.31 | 4.17 | 4.27 | 4.2725 | 2.46 |
| A&H | 4.77 | 4.78 | 4.9 | 4.96 | 4.8525 | 3.04 |
| SPEED STICK ® | 4.87 | 4.7 | 4.83 | 4.34 | 4.685 | 2.8725 |
| ARRID ™ | 4.88 | 4.66 | 4.64 | 4.74 | 4.73 | 2.9175 |
| MITCHUM ® | 3.77 | 3.67 | 3.59 | 3.54 | 3.6425 | 1.83 |
| Blank | 1.76 | 1.83 | 1.87 | 1.88 | 1.835 | |
| BRUT ® | 3.62 | 3.58 | 3.67 | 3.53 | 3.6 | 1.765 |

TABLE 2-continued

Wash Study Results

| APDO Sample | b* 1 | b* 2 | b* 3 | b* 4 | Avg b* | Delta b* |
|---|---|---|---|---|---|---|
| RG sport | 4.29 | 4.21 | 4.05 | 4.06 | 4.1525 | 2.3175 |
| RGx | 5.39 | 5.44 | 5.48 | 5.56 | 5.4675 | 3.6325 |
| Blank | 1.55 | 1.6 | 1.78 | 1.68 | 1.6525 | |
| Prototype 1 | 2.81 | 2.62 | 2.86 | 3.0 | 2.8225 | 1.17 |
| Prototype 2 | 2.73 | 2.91 | 2.75 | 2.92 | 2.8275 | 1.175 |
| Prototype 3 | 3.37 | 3.1 | 2.38 | 2.99 | 2.96 | 1.3075 |

As can be seen from the results depicted in Table 2, the antiperspirant stick prototypes prepared as described herein had lower delta b* values than any of the other antiperspirant stick compositions tested. Each of the prototypes was based on the same basic formulation, but with different fragrance components. Specifically, the prototypes were based on the formulation depicted in Table 3 below.

TABLE 3

Prototype Formulations

| Component | Wt % |
|---|---|
| Lubricant (Cyclopentasiloxane) | 25-35 |
| Primary Structurant (Stearyl Alcohol) | 16-20 |
| Secondary Structurant (Cetyl Alcohol) | 0.5-2 |
| Secondary Structurant (Synthetic Wax) | 1.5-2 |
| Melting Point Additive ($C_{12}$-$C_{15}$ Alkyl Benzoate) | 7-15 |
| Sweat-Sequestering Agent (Ceteareth-30) | 3-6 |
| Plasticizer (Propylene Carbonate) | 1-3 |
| Antiperspirant Active Agent (Aluminum Zirconium Salt) | 16-20 |
| Fragrance | Variable |

Example 2—In Vivo Staining Study

A group of panelists had 0.35 g of test formulation applied to their underarms. Test formulations included prototype formulations according to Table 3 having 16 wt % or 20 wt % antiperspirant active agent. As a comparative sample, commercially available RIGHT GUARD® XTREME™ (RGXD5) was also tested alongside the prototype formulations. Each panelist was given a white cotton t-shirt to wear for four hours after application of the product, after which the t-shirt was washed. 0.35 g of product was then re-applied to the underarms of the panelists and the t-shirt was worn for another four hours, after which the t-shirt was again washed. This process was repeated for four days for a total of 8 applications. Color was rated using b* values with a Gardner colorimeter as well as visual scores.

As can be seen in FIG. 1, both prototypes having 16 wt % or 20 wt % antiperspirant active agent had lower b* values as compared to the commercially available RGXD5 sample. Further, there was no significant difference between the 16 wt % sample and the 20 wt % sample. These results indicate that the antiperspirant stick compositions described herein can include effective amounts of antiperspirant active agents while reducing or minimizing the staining potential of the composition.

Example 3—Individual Component Wash Study

A variety of common antiperspirant stick components were combined at a level of 10 wt % in a simple base of cyclopentasiloxane and Al/Zr trichlorohydrate to determine individual discoloration effects for the various components. These test samples were applied to 100% cotton t-shirts and allowed to sit for 1 hour. Samples were then washed with PUREX® Free n Clear laundry detergent and dried at the high setting in an electric dryer. This staining washing cycle was repeated ten times for each sample. Four replicates of each sample were tested. Each of the sample compositions was compared to a control (cyclopentasiloxane and Al/Zr trichlorohydrate alone) and blank (untreated substrate that went through the wash cycles). The components tested are listed in Table 4 below along with their corresponding b* values (average of four replicates):

TABLE 4

| Stick Components | |
|---|---|
| Component | b* |
| 12-Hydroxystearic Acid | 5.47 |
| Hydrogenated Castor Oil | 4.80 |
| Petrolatum | 3.55 |
| Polyethylene | 3.53 |
| $C_{12}$-$C_{15}$ Alkyl Benzoate | 3.04 |
| PPG-14 Butyl Ether | 2.63 |
| Myristyl Myristate | 2.65 |
| Kester Wax | 2.55 |
| Cetyl Alcohol | 2.51 |
| Ceteareth-20 | 2.50 |
| Stearyl Alcohol | 2.43 |
| Talc | 2.46 |
| Control | 2.08 |
| Blank | 1.98 |

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. An antiperspirant stick composition, comprising:
   1.5 to 2.0 wt % of a synthetic wax having a melting point of less than or equal to 90° C.;
   5 wt % to 20 wt % of a melting point additive present at a weight ratio to the synthetic wax to provide the composition with a melting point greater than or equal to 40° C.;
   an effective amount of an antiperspirant active agent; and less than 1 wt % hydrogenated oils, petrolatum, 12-hydroxystearic acid, polyethylenes having a melting point greater than or equal to 60° C., and combinations thereof,
      wherein the weight ratio of the melting point additive to the synthetic wax is 4:1 to 8:1.

2. The composition of claim 1, wherein the synthetic wax has a weight average molecular weight (Mw) of from 100 g/mol to 2000 g/mol.

3. The composition of claim 1, wherein the synthetic wax has a melting point less than or equal to about 80° C.

4. The composition of claim 1, wherein the synthetic wax has a viscosity of from about 0.1 centipoise (cps) to about 20 cps at a temperature of 99° C.

5. The composition of claim 1, wherein the synthetic wax has a penetration value of from about 8 decimillimeters (dmm) to about 30 dmm at 25° C.

6. The composition of claim 1, wherein the synthetic wax has less than 10% branching.

7. The composition of claim 1, wherein the melting point additive is a member selected from the group consisting of $C_{12}$-$C_{15}$ alkyl benzoates, mineral oil, dimethicone, and combinations thereof.

8. The composition of claim 1, wherein the melting point additive is present at a weight ratio to the synthetic wax to provide the composition with a melting point greater than or equal to 45° C.

9. The composition of claim 1, wherein the melting point additive is present in the composition in an amount from about 8 wt % to about 12 wt %.

10. The composition of claim 1, wherein the antiperspirant active agent is a member selected from the group consisting of aluminum chlorohydrate, aluminum chloride, aluminum hydroxide, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate polyethylene glycol, aluminum sesquichlorohydrate propylene glycol, aluminum-zirconium octachlorohydrate, aluminum-zirconium octachlorohydrex glycine, aluminum-zirconium pentachlorohydrate, aluminum-zirconium pentachlorohydrex glycine, aluminum-zirconium tetrachlorohydrate, aluminum-zirconium tetrachlorohydrex glycine, aluminum-zirconium trichlorohydrate, aluminum-zirconium trichlorohydrex glycine, potassium aluminum sulfate, aluminum undecylenoyl collagen amino acid, sodium aluminum lactate, aluminum sulfate, sodium aluminum chlorohydroxylactate, aluminum bromohydrate, aluminum chlorohydroxyallantoinate, zinc chloride, zinc sulfocarbolate, zinc sulfate, zirconium chlorohydrate, and combinations thereof.

11. The composition of claim 1, wherein the antiperspirant active agent is present in the composition in an amount from about 14 wt % to about 20 wt %.

12. The composition of claim 1, further comprising a lubricant.

13. The composition of claim 12, wherein the lubricant is a member selected from the group consisting of cyclopentasiloxane, cyclohexasiloxane, dimethylpolysiloxane, methylphenylpolysiloxane, hexamethyldisiloxane, octamethyltrisiloxane, decamethyltetrasiloxane, and combinations thereof.

* * * * *